(12) United States Patent
Steinbrenner et al.

(10) Patent No.: US 7,161,039 B2
(45) Date of Patent: Jan. 9, 2007

(54) METHOD AND DEVICE FOR PRODUCING ETHYLAMINE AND BUTYLAMINE

(75) Inventors: Ulrich Steinbrenner, Neustadt (DE); Frank Funke, Mannheim (DE); Ralf Böhling, Griesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 315 days.

(21) Appl. No.: 10/495,278

(22) PCT Filed: Nov. 12, 2002

(86) PCT No.: PCT/EP02/12609

§ 371 (c)(1),
(2), (4) Date: May 11, 2004

(87) PCT Pub. No.: WO03/042157

PCT Pub. Date: May 22, 2003

(65) Prior Publication Data

US 2005/0124832 A1    Jun. 9, 2005

(30) Foreign Application Priority Data

Nov. 12, 2001 (DE) ................................. 101 55 524

(51) Int. Cl.
*C07C 209/60* (2006.01)
(52) U.S. Cl. ..................................................... 564/485
(58) Field of Classification Search ..................... None
See application file for complete search history.

(56) References Cited

U.S. PATENT DOCUMENTS

| 2,501,556 | A | 3/1950 | Withman |
| 2,750,417 | A | 6/1956 | Closson et al. |
| 4,302,603 | A | 11/1981 | Pez |
| 4,336,162 | A | 6/1982 | Pez |
| 5,763,668 | A | 6/1998 | Dingerdissen |
| 6,576,796 | B1 | 6/2003 | Funke et al. |

FOREIGN PATENT DOCUMENTS

| DE | 100300619 | 1/2002 |
| DE | 10041676 | 3/2002 |
| FR | 1484782 | 5/1966 |

OTHER PUBLICATIONS

J. Am. Chem.Soc. 76 (1954) pp. 1895-1902.

*Primary Examiner*—Brian Davis
(74) *Attorney, Agent, or Firm*—Novak Druce & Quigg, LLP (57) ABSTRACT

A process for preparing ethylamines, butylamines and mixed ethyl/butylamines comprising the following steps:
 (i) Hydroamination of butadiene and ethylene by means of a monoalkylamine and/or a dialkylamine in which alkyl=ethyl and/or butyl in the presence of an alkali metal amide as catalyst,
 (ii) isomerization of the amines obtained in the hydroamination (i), if appropriate under the following conditions:
  (iia) prior fractionation into particular fractions and/or
  (iib) isomerization under hydrogenating conditions and/or
  (iic) isomerization in the presence of ammonia,
 (iii) fractionation of the resulting product mixture with isolation of the desired product amines and recycle of the amines suitable as starting material to step (i).

25 Claims, 1 Drawing Sheet

FIG: 1

METHOD AND DEVICE FOR PRODUCING ETHYLAMINE AND BUTYLAMINE

This application is a 371 of PCT/EP02/12609 filed Nov. 12, 2002.

The present invention relates to a process for preparing ethylamines and butylamines.

Ethylamines and butylamines serve as starting materials for the preparation of surfactants, textile and flotation auxiliaries, bactericides, corrosion and foam inhibitors, additives for pharmaceuticals and also as antioxidants for fats and oils. These amines can be prepared by hydrogenation of the corresponding nitriles or nitro compounds, by reductive amination of appropriate aldehydes and ketones and by amination of appropriate alcohols. In particular, they are prepared on an industrial scale by amination of the corresponding alcohol or the corresponding carbonyl compound over metal catalysts, which may be supported or unsupported, under hydrogenative conditions.

The use of aldehydes, ketones and nitriles and also of alcohols, i.e. ethanol and butanol in the present case, as starting materials for the preparation of alkylamines is in principle uneconomical compared to the use of the corresponding olefins, i.e. ethene and butene, because of the price of the starting materials.

An alternative way of preparing the amines mentioned is the addition of $NH_3$ or amines onto olefins in the presence of acid catalysts, for example zeolites, basic catalysts, for example metal amides, in particular alkali metal and alkaline earth metal amides, amides of transition group IV, alkali metal alkoxides or of transition metal complexes.

However, this hydroamination of olefins suffers from a series of difficulties which frequently stand in the way of industrial implementation of the reaction. Examples are indicated below.

Thus, in the $NaNH_2$ or $KNH_2$ catalyzed addition of $NH_3$ onto olefins, as is described, for example, in B. W. Howk et al., J. Am. Chem. Soc. 76 (1954), 1899–1902 and R. D. Closson et al., U.S. Pat. No. 2,750,417, the space-time yields of the desired alkylamines are very small even at high temperatures and olefin pressures because of the low activity and solubility of the metal amide. U.S. Pat. No. 4,336,162 and U.S. Pat. No. 4,302,603 describe a starting point for solving this problem by changing to rubidium and cesium amides or using a eutectic of $NaNH_2$ and $KNH_2$. In the first case, industrial implementation is prohibited by the extremely high catalyst price, while in the second case, the space-time yields of the desired alkylamines are always too small.

The hydroamination of olefins using secondary amines in the presence of acid catalysts generally proceeds in poorer yields and with poorer selectivities than the corresponding hydroamination using ammonia or primary amines.

It is an object of the present invention to provide a process by means of which ethylamines and butylamines and also mixed ethyl/butylamines can be prepared in one process and the desired amounts of ethylamine and butylamine prepared can be controlled.

We have found that this object is achieved by a process for preparing ethylamines, butylamines and mixed ethyl/butylamines, which comprises the following steps:

(i) Hydroamination of butadiene and ethylene by means of a monoalkylamine and/or a dialkylamine in which alkyl=ethyl and/or butyl in the presence of an alkali metal amide as catalyst, (ii) isomerization of the amines obtained in the hydroamination (i), if appropriate under the following conditions:
  prior fractionation into particular fractions and/or
  isomerization under hydrogenating conditions and/or
  isomerization in the presence of ammonia, (iii) fractionation of the resulting product mixture with isolation of the desired product amines and recycle of the amines suitable as starting material to step (i) and, if desired, to step (ii).

The process of the present invention allows the preparation of ethyl- and butyl-substituted organic amines, in particular triethylamine and tributylamine, in a combined process whose net reaction comprises, in a preferred embodiment, the reaction of hydrogen, ammonia, ethylene and butadiene to form the amines mentioned. As starting material for the first reaction step, preference is given to using diethylamine, dibutylamine and/or ethylbutylamine, where these latter amines can also be formed fresh in the course of the process of the present invention and be recirculated to the reaction.

The patent applications DE 10 030 619.5 and DE 10 041 676.4 by the present applicant, which are not prior publications, describe a general process for preparing amines by hydroamination of olefins. In this process, an olefin is reacted a) with a primary amine or with a secondary amine in the presence of a metal monoalkylamide or metal dialkylamide as catalyst or b) with ammonia or a primary amine in the presence of a solid inorganic acid as catalyst or c) with ammonia, a primary amine or a secondary amine in the presence of a transition metal complex as catalyst in a first process step and the hydroamination product or products obtained are reacted in a second process step at from 80 to 400° C. either in the presence of a transalkylation catalyst or in the presence of hydrogen and a transalkylating hydrogenation or dehydrogenation catalyst.

These applications do not disclose the use of ethylene and butadiene together in one process for preparing the corresponding ethyl- and butyl-containing amines.

The process of the present invention is described in more detail below.

In the first process step, butadiene and ethylene are reacted with a monoalkylamine and/or a dialkylamine in which alkyl=ethyl and/or butyl under hydroaminating conditions. The addition of butadiene onto the amine forms a butenyl-containing amine, while the addition of ethylene forms an ethyl-containing amine.

The relative amounts of the olefins to be hydroaminated (partial pressures) and the type and amount of the amines enable the distribution of the products formed to be controlled.

When a dialkylamine is employed, it is possible to use an amine having mixed substitution. For example, use of diethylamine as amine results in formation of diethylbutenylamine and triethylamine, use of monoethylamine results in formation of ethyldibutenylamine, diethylbutenylamine and triethylamine, use of dibutylamine results in formation of dibutylbutenylamine and ethyldibutylamine, use of butylamine results in formation of butyldibutenylamine, butyldiethylamine and butylbutenylethylamine. Furthermore, the use of the olefins in a deficiency relative to the amine used results in a mixture which further comprises secondary and/or primary amines being obtained after the hydroamination.

When the process of the present invention is to be used to prepare product mixtures comprising mainly ethylamine, in particular triethylamine, a high proportion of ethylene and/or ethylamine or diethylamine is used in the hydroamination reaction. If a high proportion of butylamines, mainly tributylamine, is to be obtained, a high proportion of butadiene and/or butylamine or dibutylamine is used.

The hydroamination of the present invention is generally carried out so that the amine and the olefin which give the alkylamine which is to be preferably prepared are used in excess over the other starting materials or are even used exclusively. In this case, the amine can also be used as sole starting amine.

Preferred amines which are used in the process of the present invention are diethylamine, dibutylamine and butylethylamine, in particular diethylamine. Preference is given to adding a distinct excess of ethylene.

In one embodiment of the present invention, the hydroaminations of the ethylene and of the butadiene are not carried out in a single reaction step, but instead in two successive steps. Here, the order of the hydroaminations is immaterial; thus, the reaction of the amine with butadiene can be carried out first and the reaction with ethylene can be carried out subsequently, or vice versa. Carrying out the hydroamination in two separate steps has the advantage that the desired amount of products relative to one another can be controlled more readily than in the case of a single-stage process in which this is possible virtually only via the partial pressures of the two olefins.

The hydroamination of ethylene and butylene is carried out using amides of the alkali metals as catalysts.

Amides which can be used here are salts of Li, Na, K, Rb or Cs, preferably of Li, Na or K, in particular of Na.

The amides which can be used according to the present invention are derived from primary or secondary amines. These amines can have any suitable substituents. These substituents are generally selected from the group consisting of linear and branched, cyclic and acyclic aliphatic and olefinic hydrocarbons which may bear one or more substituents from the group consisting of phenyl, amino and alkoxy groups. The hydrocarbons mentioned are preferably aliphatic cyclic or acyclic hydrocarbons having from 1 to 12 carbon atoms. Examples of amines which can be used for preparing the amide include methylamine, dimethylamine, ethylamine, diethylamine, N-propylamine, di-n-propylamine, i-propylamine, di-i-propylamine, butylamine and dibutylamine. Amines and amides having mixed substituents can also be used.

It is also possible to use cyclic amines, for example pyrrolidine, piperidine, piperazine or morpholine, for preparing the amide.

Preference is given to using secondary aliphatic amines for preparing the amide catalyst, with examples being dimethylamine, diethylamine, di-i-propylamine, di-n-propylamine, di-n-butylamine, di-i-butylamine and di-sec-butylamine.

Even greater preference is given to using secondary amides which are derived from amines which are reacted with ethylene and/or butadiene in the hydroamination reaction carried out according to the present invention.

Even greater preference still is given to using diethylamide, dibutylamide and/or ethylbutylamide as amide. In particular, diethylamide is used.

The metal amides can be used as such, for instance in the form of a solution, in the reaction according to the present invention, with the metal amides being able to come from any source.

In a preferred embodiment of the present invention, the metal amide is, prior to use in the reaction, prepared from the corresponding amine which is also reacted with the olefin, preferably diethylamine, dibutylamine and/or ethylbutylamine, in particular diethylamine. The preparation of the metal amides is carried out by methods known from the literature. These are described, for example, in Houben-Weyl Methoden der organischen Chemie, $4^{th}$ edition, Volume XI/2, Thieme Verlag, Stuttgart, pages 182ff, U.S. Pat. No. 4,595,779, WO-A 93/14061, DE-A 21 17 970 Deutsches Reichspatent 615,468, GB-A 742 790, DE-A 26 13 113, U.S. Pat. No. 2,750,417, J. Wollensak, Org. Synth. 43 (1963), pages 45 ff and C. A. Brown, J. Am. Chem. Soc. 95 (1973), pages 982 ff. In general, the preparation of the amide comprises reacting a metal with the corresponding amine in the presence of an unsaturated compound, for example butadiene, isoprene, naphthalene, pyridine or styrene as electron transferrer, reacting a metal amide or hydride with the corresponding amine or reacting an organometallic compound, for example n-BuLi, MeLi, PhNa, $Et_2Mg$ or $Et_4Zr$, with the corresponding amine.

The above-described catalyst systems which are suitable for carrying out the reaction of the present invention can be used in solution, as a suspension or in supported form.

If the metal amide is, as described, prepared prior to use in the reaction, this is preferably achieved by reacting the corresponding amine with the corresponding metal, which in the most preferred embodiment is Na. For this purpose, the Na is generally dispersed in the corresponding amine, but it can also be dispersed in an inert solvent, for example a petroleum fraction, before addition of the amine. A further possibility is to disperse the alkali metal in the product amine or amines and to add the appropriate amine. If desired, a separate apparatus is used for the dispersion procedure, for example a stirred vessel, a nozzle or a reaction mixing pump. The reaction to form the amide salt proceeds in the presence of a suitable unsaturated compound, for example butadiene, isoprene, naphthalene, pyridine or styrene. In a particularly preferred embodiment of the present invention, butadiene is used as unsaturated compound. This has the advantage that, owing to the presence of butadiene which is hydroaminated according to the present invention by reaction with the amine, no additional unsaturated compound has to be added in the preparation of the amide.

In the preparation of the amide using sodium, the latter is generally placed in the reaction vessel in the form of fine particles. The particles preferably have a size distribution such that 50% by weight of the particles have a size of <1000 μm, more preferably <300 μm, in particular <100 μm.

In the preparation of the amide catalyst from the elemental metal, preferably Na, a temperature of from 0 to 150° C., preferably from 20 to 90° C., in particular from 30 to 70° C., and a pressure of from 1 to 200 bar, preferably from 1 to 100 bar, in particular from 3 to 50 bar, are employed. The preparation of the amide can be carried out batchwise, semicontinuously or continuously.

After the catalyst has been made available, butadiene and ethylene are reacted with the respective amine. This gives a mixture of amines having ethyl, butyl and/or butenyl substituents.

The relative amount of the organic amines formed can be controlled via the amount of starting materials. After the hydroamination is complete, the mixture of the organic amines is fractionated as described below.

As regards the way in which the hydroamination reaction is carried out, there are a number of variants. For example the hydroamination of butadiene can be carried out first, followed by the hydroamination of ethylene. However, it is also possible to carry out both hydroamination reactions in one reaction zone as a single-vessel synthesis. The hydroamination reaction can in each case also be coupled with the preparation of the catalyst.

In the hydroamination reactions, it is also possible for inert alkylamines such as triethylamine, tributylamine, butyldiethylamine and dibutylethylamine or saturated hydrocarbons to be present in the reactor.

In a preferred embodiment of the present invention, the preparation of the amide and the hydroamination of the butadiene are carried out in a single process step. The hydroamination of the ethylene is carried out subsequent thereto.

In this embodiment, it is advantageous to react butadiene firstly with the amine to be alkylated, preferably diethylamine, dibutylamine and/or butylethylamine, in particular diethylamine, in the presence of the amount of Na required to form the necessary amount of amide. The presence of butadiene results in the formation of the amide occurring spontaneously. A further electron transferrer can also be added, but this is not preferred. The excess of the amine which is not reacted with the Na to form the amide reacts with the butadiene to form butene-containing amines. These are, for example, butenyldiethylamine, butenyldibutylamine and/or butenylbutylethylamine. The hydroamination of butadiene according to the present invention forms mainly linear butenyl radicals in which the olefinic double bond is generally in the γ position relative to the N atom. However, double bond isomerization can also result in the double bond being located in the α, β or δ position relative to the N atom. Branched butenyl radicals are generally not formed or formed only in minor amounts.

The amount of Na used in the preparation of the amide is chosen so that the molar ratio of Na to the total amount of olefin (butadiene plus ethylene) is from 1:5 to 1:300, preferably from 1:10 to 1:200, in particular from 1:50 to 1:150.

If the preparation of the amide and the hydroamination of butadiene are carried out in combination as described above, this occurs at from 0 to 150° C., preferably from 20 to 90° C., in particular from 30 to 70° C., and at pressures of from 1 to 200 bar, preferably from 1 to 100 bar, in particular from 3 to 50 bar.

In place of 1,3-butadiene, it is also possible to use 1,3-butadiene-containing hydrocarbons, for example $C_4$ fractions as are obtained, for example, in the cracking of naphtha, in the dehydrogenation of LPG or LNG or in the Fischer-Tropsch synthesis.

Subsequent to the above-described butadiene hydroamination, the resulting reaction mixture is reacted with ethylene. In this step, not yet completely substituted amines are ethylated. This gives, for instance in the case of the preferred use of dibutylamine, butylethylamine and/or diethylamine, the products dibutylethylamine, butyldiethylamine and/or triethylamine. If primary amines are used in the preceding step of butadiene hydroamination, the reaction with ethylene also forms amines which contain ethyl and butenyl substituents. Optionally, further diethylamine or monoethylamine can additionally be introduced into the reactor, likewise inert trialkylamines.

The relative amounts of the various amines which are formed can be regulated via the type and amount of the starting materials, for example the amount of butadiene used in the butadiene hydroamination or the amount of further incompletely alkylated amine which is optionally added afterwards.

In most cases, the main desired product will be triethylamine. In this case, an excess of ethylene over butadiene will be used. The excess of ethylene and, if appropriate, also the amount of amine, in particular diethylamine, is preferably set so that triethylamine is formed in a 5–20-fold excess over butyl-/butenyl-containing amines, in particular an 8–12-fold excess.

The above-described hydroamination of ethylene is carried out at from 30 to 180° C., preferably from 50 to 100° C., and at pressures of from 1 to 200 bar, preferably from 20 to 200 bar, in particular from 30 to 50 bar.

In a further embodiment of the present invention, the hydroaminations of butadiene and of ethylene are carried out in a single reaction step. In particular, this reaction step also includes the preparation of the amide catalyst. In this case, the process is carried out at from 30 to 180° C., preferably from 50 to 100° C., at pressures of from 1 to 200 bar, preferably from 30 to 50 bar. However, the amide catalyst can also be prepared separately, but this is not preferred.

In all the above-described reaction variants, the reaction of the olefin with the amine in the presence of the amide is carried out in a manner known to those skilled in the art. A description of preferred ways of carrying out the reaction may be found in G. P. Pez et al., Pure and Applied Chemistry 57 (1985), pages 1917–26, R. D. Closson et al., J. Org. Chem. 22 (1957), pages 646–9, U.S. Pat. No. 2,501,556, D. Steinborn et al., Z. Chem. 29 (1989), pages 333–4, D. Steinborn et al., Z. Chem. 26 (1986), pages 349–59 and H. Lehmkuhl et al., J. Organomet. Chem. 55 (1973), pages 215–20. The reaction of the olefin with the amine in the presence of the metal alkylamide can also be carried out in the presence of small amounts of ammonia, generally <1 mol % based on the amines used, as described, for example, in DE-A 21 17 970.

The metal alkylamide can, as described in DE-A-26 13 113, be transformed during the reaction into a metal hydride by β-elimination or action of $H_2$, forming an imine in the case of the β-elimination. This hydride can be converted in the presence of a primary or secondary amine back into metal alkylamide and $H_2$ as described in DE-A 26 13 113, C. A. Brown, J. Am. Chem. Soc. 95(3) (1973), 982ff or C. A. Brown, Synthesis (1978), 754ff, so that the metal hydride may be regarded as a type of "rest form" of the metal alkylamide. It is therefore equivalent to the metal alkylamide for the purposes of the present invention.

Furthermore, complexing agents may be present as solvents both in the preparation of the catalyst and in the reaction.

Thus, for example, J. F. Remenar (J. Am. Chem. Soc. 120 (1988), 4081ff), H. Lehmkuhl et al., (J. Organomet. Chem. 55 (1973), 215ff and D. Steinborn et al., (Z. Chem. 29 (1989), 333ff, describe the use of N,N,N',N'-tetramethylethylenediamine, N,N,N',N'',N''-pentamethyldiethylenetriamine, N,N,N',N'-tetramethylcyclohexanediamine and tetrahydrofuran as complexing agents.

It is also possible to add amines having a plurality of amine nitrogen atoms per molecule, e.g. N,N,N',N'-tetraethylethylenediamine, N-permethylated or N-perethylated triethylenetetramine through to N-permethylated or N-perethylated polyimine having molar masses up to 500 000 dalton, ethers and polyethers such as diglyme, triglyme and the corresponding homologues, end-capped polyols, e.g. PEG, PPG, polyTHF, and complexing agents containing amine nitrogen and ethyl oxygen atoms in the molecule, e.g. 3-methoxyethylamine, 3-(2-methoxyethoxy)propylamine or bis(N,N'-dimethylaminoethyl)ether, to the reaction mixture.

The catalyst can be present as a solution, as a suspension or in supported form on a typical catalyst support such as $SiO_2$, $Al_2O_3$, $TiO_2$, $ZrO_2$, activated carbon, MgO, $MgAl_2O_4$. The catalyst is preferably present as a solution or suspension, particularly preferably as a solution.

The hydroamination of butadiene and/or ethylene can be carried out batchwise, (addition of the olefin to the catalyst and amine), semicontinuously (addition of the olefin to the reaction mixture) or continuously (addition of all components).

In each case, preference is given to a molar ratio of olefin:secondary amine of from 3:1 to 1:10, particularly preferably 1:1 to 1:2.

The ratio of olefin:primary amine is preferably from 6:1 to 1:5, particularly preferably from 2:1 to 1:1.

Possible reactors are all typical reaction apparatuses, e.g. stirred tanks, loop reactors, bubble columns, packed bubble columns, cascaded bubble columns and stirred columns.

Subsequent to the hydroamination reaction, the catalyst is separated from the reaction mixture. This is carried out by customary methods, for example distillation under reduced or atmospheric pressure, filtration, membrane filtration, sedimentation, washing with water, preferably acids, salt solutions or alcohol.

Nonprotolyzed catalyst (metal alkylamide or metal hydride) can subsequently be returned to the reaction.

Nonhydrolyzed catalyst is returned to the hydroamination reaction. It is preferably recycled to the hydroamination of ethylene if this reaction is carried out as a separate step.

In one variant of the present invention, unreacted butadiene, ethylene and any butenes formed are separated off together with the catalyst.

The next step of the process of the present invention is the isomerization, if appropriate under hydrogenating conditions and/or with addition of $NH_3$, of the amines which have been obtained in the preceding hydroamination reactions. This isomerization can precede fractionation of the amines. In any case, fractionation of the amines is carried out after the isomerization. Part of the amines obtained after isomerization/fractionation is then returned to the hydroamination reaction with ethylene and/or butadiene. The type of isomerization and when it is carried out and how the reaction mixture formed in the hydroamination and the reaction mixture obtained after isomerization are fractionated depends on the desired product spectrum.

In the simplest case, the mixture obtained after the hydroamination of the amine with butadiene and ethylene, which comprises various butyl-, butenyl- and/or ethyl-substituted alkylamines, is subjected to an isomerization which, owing to the presence of butenyl groups in the amine, is carried out under hydrogenating conditions. A transalkylating hydrogenation or dehydrogenation catalyst is used in this isomerization. In the isomerization, the product spectrum of the amines formed can be shifted to a larger proportion of one or more particular desired amine(s). $NH_3$ can optionally be added. Addition of $NH_3$ effects the formation of secondary and/or primary amines which are preferably reused as starting amines.

However, in a preferred embodiment of the present invention, amines containing butyl and/or butenyl groups can be separated off prior to the isomerization/hydrogenation. This fraction is subsequently hydrogenated and isomerized with transalkylation. In a variant of this preferred embodiment, $NH_3$ is introduced in this isomerization/hydrogenation, so that primary and secondary butyl-containing amines are also formed. This results in butylamines which may, depending on the previous reaction conditions, contain one or two ethyl substituents when mixed ethyl- and butyl-substituted amines (and not exclusively butyl-substituted amines) are used. The transalkylation is carried out using the conditions and catalysts known to those skilled in the art. The desired products, preferably tributylamine, are generally separated off, either before or after the transalkylation. The secondary and primary butyl-substituted amines are then either recycled as starting materials or are once again transalkylated under isomerizing conditions to form more tributylamine.

The mixture comprising triethylamine, diethylamine and possibly monoethylamine which is obtained after the butyl-/butenyl-substituted amines have been separated off is fractionated. This is preferably carried out by distillation. This fractionation gives the desired product, which is generally triethylamine. All or some of the triethylamine is taken off from the process.

This fractionation also gives a mixture which is returned as starting material to the hydroamination reaction, either directly or after isomerizing transalkylation.

As mentioned above, a monoalkylamine or dialkylamine containing at least one ethyl or butyl substituent is used as starting material in the hydroamination reaction. A secondary amine or a mixture of secondary amines is preferably used as starting material. Preferred starting materials are diethylamine, dibutylamine or ethylbutylamine or a mixture comprising one or more of these amines. In particular, diethylamine is used.

Depending on which amine or amines is/are to be recycled as starting material to the hydroamination, the amine mixtures obtained after the catalyst has been separated off are fractionated and, if appropriate with addition of ammonia, transalkylated under isomerizing conditions. After the mixture has been fractionated again if necessary, part of the amines formed is recycled as starting material.

The transalkylation, which is carried out under conditions known to those skilled in the art, thus provides starting amines for the hydroamination. The transalkylation step is generally carried out under a hydrogen atmosphere. Although such an atmosphere is not absolutely necessary, it increases the activity and life of the catalyst used.

The transalkylation is carried out using conditions and catalysts known to those skilled in the art. The composition of the starting mixture fed in depends, as mentioned above, on the amine to be used as starting material for the hydroamination. Preference is given to using triethylamine, diethylamine as starting material for the transalkylation reaction. In particular, triethylamine and/or diethylamine are/is used.

The transalkylation reaction is preferably carried out with addition of $NH_3$, which enables a high proportion of secondary amines in the product mixture from the transalkylation to be achieved.

The above-described transalkylation of the amines can in principle be carried out either with or without addition of $NH_3$. When $NH_3$ is excluded, virtually no additional secondary and/or primary amines are generated. The amine mixture obtained in the hydroamination is in this case finally converted into tertiary amines, preferably triethylamine and tributylamine. The tertiary homosubstituted amines can easily be separated from one another by distillation, i.e. generally triethylamine from tributylamine. The other amines are recirculated to form the desired homosubstituted tertiary amines. In this way, the overall result is to form the desired tertiary amines, preferably triethylamine and tributylamine, from the amines introduced into the hydroamination.

The isomerization/hydrogenation step can, if desired, be configured as a reactive distillation. In this embodiment, too, depending on the desired way in which the reaction is to be carried out, all amines obtained after the hydroamination may be present. The butenyl-/butyl-containing amines can also, if appropriate, have been separated off from the other amines before one of the fractions obtained, if appropriate after further prior fractionation, or else both fractions are subjected to the isomerization/transalkylation configured as a reactive distillation.

The above-described transalkylation reaction of the amines is carried out at from 80 to 400° C.

In particular, the reaction of the hydroamination product under transalkylating conditions can be carried out as described, for example, in Houben Weyl, Volume XI/1, nitrogen compounds II, 1957, Georg Thieme Verlag Stuttgart, pp. 248 to 261.

Accordingly, the amine transalkylation ("amine exchange") is carried out in the presence of dehydration catalysts and hydrogenation/dehydrogenation catalysts.

Dehydration catalysts suitable as transalkylation catalyst are, for example, manganese(II) oxide/activated carbon, aluminum silicates, $Al_2O_3$, $TiO_2$ or $ZrO_2$.

To maintain the catalytic activity, the presence of hydrogen is advantageous. Alternatively, the hydrogenation or dehydrogenation catalyst can be freed of deposits by reduction with $H_2$ at regular intervals.

Catalysts suitable as hydrogenation and dehydrogenation catalysts are ones which comprise, as catalytically active constituents, elements from the group consisting of copper, silver, gold, iron, cobalt, nickel, rhenium, ruthenium, rhodium, palladium, osmium, iridium, platinum, chromium, molybdenum and tungsten, in each case in metallic form (oxidation state 0) or in the form of compounds such as oxides which are reduced to the corresponding metal under the process conditions.

The catalytically active constituents copper, silver, gold, iron, cobalt, nickel, rhenium, ruthenium, rhodium, palladium, osmium, iridium, platinum, chromium, molybdenum and/or tungsten are generally present in total amounts of from 0.1 to 80% by weight, preferably from 0.1 to 70% by weight, particularly preferably from 0.1 to 60% by weight, calculated as metal in the oxidation state 0, in the catalytically active composition of the catalyst.

Preference is given to catalysts comprising, as catalytically active constituents, elements selected from the group consisting of copper, silver, cobalt, nickel, ruthenium, rhodium, palladium, platinum, chromium and molybdenum, in particular selected from the group consisting of copper, cobalt, nickel, in each case in metallic form (oxidation state 0) or in the form of compounds such as oxides which are reduced to the corresponding metal under the process conditions.

Greater preference is given to catalysts which comprise the catalytically active constituents copper, silver, iron, cobalt, nickel, ruthenium, rhodium, palladium, osmium, iridium and/or platinum and a support material preferably selected from the group consisting of aluminum oxide, zirconium dioxide, titanium dioxide, carbon and/or oxygen-containing compounds of silicon.

The catalytically active composition of these catalysts which are preferably used in the process of the present invention generally comprises the catalytically active constituents copper, silver, iron, cobalt, nickel, ruthenium, rhodium, palladium, osmium, iridium and/or platinum in a total amount of from 0.1 to 80% by weight, preferably from 0.1 to 70% by weight, particularly preferably from 0.1 to 60% by weight, calculated as metal in the oxidation state 0.

Furthermore, the catalytically active composition of these catalysts which are preferably used generally comprises the support materials aluminum oxide ($Al_2O_3$), zirconium dioxide ($ZrO_2$), titanium dioxide ($TiO_2$), carbon and/or oxygen-containing compounds of silicon, calculated as $SiO_2$, in a total amount of from 20 to 99.9% by weight, preferably from 30 to 99.9% by weight, particularly preferably from 40 to 99.9% by weight.

Particular preference is given to catalysts comprising the active components Cu, Co, Ni and/or Pd, in particular Cu, Co and/or Ni. These can be used as unsupported (all active) catalysts or as supported catalysts.

Very particular preference is given to Cu-containing catalysts which, as recognized according to the present invention, are more selective because of their comparatively low ethane or methane formation.

Examples are copper alloys, metallic copper, e.g. in the form of copper mesh, and Cu catalysts having a Cu content of from 2 to 70% by weight of Cu, calculated as CuO, on a support, preferably comprising from 10 to 55% by weight of Cu, calculated as CuO, on a support. Preferred support materials are aluminum oxide ($Al_2O_3$) zirconium dioxide ($ZrO_2$), titanium dioxide ($TiO_2$), carbon and/or oxygen-containing compounds of silicon.

Examples of catalysts which can be used in the process of the present invention are those disclosed in EP-A 382 049, whose catalytically active composition comprises, prior to treatment with hydrogen, from 20 to 85% by weight, preferably from 70 to 80% by weight, of $ZrO_2$, from 1 to 30% by weight, preferably from 1 to 10% by weight of CuO and from 1 to 40% by weight each, preferably from 5 to 20% by weight each, of CuO and NiO, for example the catalysts described in loc. cit. on page 6 which have the composition 76% by weight of Zr, calculated as $ZrO_2$, 4% by weight of Cu, calculated as CuO, 10% by weight of Co, calculated as CoO, and 10% by weight of Ni, calculated as NiO.

Furthermore, the catalysts disclosed in EP-A 963 875, whose catalytically active composition prior to treatment with hydrogen comprises from 22 to 40% by weight of $ZrO_2$, from 1 to 30% by weight of oxygen-containing compounds of copper, calculated as CuO, from 15 to 50% by weight of oxygen-containing compounds of nickel, calculated as NiO, with the molar Ni:Cu ratio being >1, from 15 to 50% by weight of oxygen-containing compounds of cobalt, calculated as CoO, from 0 to 10% by weight of oxygen-containing compounds of aluminum and/or manganese, calculated as $Al_2O_3$ and $MnO_2$, and no oxygen-containing compounds of molybdenum, for example the catalyst A disclosed in loc. cit., page 17, which has the composition 33% by weight of Zr, calculated as $ZrO_2$, 28% by weight of Ni, calculated as NiO, 11% by weight of Cu, calculated as CuO, and 28% by weight of Co, calculated as CoO, can be used in the process of the present invention.

In addition, the catalysts disclosed in EP-A 514 692, whose catalytically active composition prior to treatment with hydrogen comprises from 5 to 100% by weight of an oxide of copper and nickel in an atomic ratio of from 1:1 to 10:1, preferably from 2:1 to 5:1, and zirconium oxide and/or aluminum oxide, in particular the catalysts disclosed in loc. cit. on page 3, whose catalytically active composition before treatment with hydrogen comprises from 20 to 80% by weight, particularly preferably from 40 to 70% by weight, of $Al_2O_3$ and/or $ZrO_2$, from 1 to 30% by weight of CuO, from 1 to 30% by weight of NiO and from 1 to 30% by weight of CoO, can be used in the process of the present invention.

Preference is given to using the catalysts disclosed in the following patent applications:

Catalysts disclosed in DE-A 19 53 263 comprising cobalt, nickel and copper and aluminum oxide and/or silicon dioxide and having a metal content of from 5 to 80% by weight, in particular from 10 to 30% by weight, based on the total catalyst, where the catalysts comprise, calculated on the basis of the metal content, from 70 to 95% by weight of a mixture of cobalt and nickel and from 5 to 30% by weight of copper and the weight ratio of cobalt to nickel is from 4:1 to 1:4, in particular from 2:1 to 1:2;

catalysts disclosed in EP-A 696 572, whose catalytically active composition prior to reduction with hydrogen comprises from 20 to 85% by weight of $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/or manganese, calculated as $Al_2O_3$ and $MnO_2$, for example the catalyst disclosed in loc. cit., page 8, which has the composition 31.5% by weight of $ZrO_2$, 50% by weight of NiO, 17% by weight of CuO and 1.5% by weight of $MoO_3$;

catalysts which are disclosed in EP-A 284 919 and have the formula $M_xMg_y(SiO_2) \cdot nH_2O$, where M is a divalent, reducible metal atom from the group consisting of Cu, Fe, Co and Ni, x and y are numbers which together may reach the value 1.5 and n after drying, expressed in % by weight, is from 0 to 80, for example the catalyst described in loc. cit. in the example, which comprises 35% of CuO, 9% of MgO and 38% of $SiO_2$, and the catalyst which is described in EP-A 863 140 on page 3 and comprises from 45 to 47% by weight of CuO, magnesium silicate comprising about 15 to 17% by weight of MgO and from 35 to 36% by weight of $SiO_2$, about 0.9% by weight of $Cr_2O_3$, about 1% by weight of BaO and about 0.6% by weight of ZnO;

catalysts described in DE-A 24 45 303 which are obtainable by heating a basic copper- and aluminum-containing carbonate of the composition $Cu_mAl_6(CO)_{0.5m}O_3(OH)_{m+12}$, where m is any, not necessarily integral, value in the range from 2 to 6, at from 350 to 700° C., for example the copper-containing precipitated catalyst which is disclosed in loc. cit., Example 1, and is prepared by treatment of a solution of copper nitrate and aluminum nitrate with sodium bicarbonate and subsequent washing, drying and heat treatment of the precipitate; and the supported catalysts which are disclosed in WO 95/32171 and EP-A 816 350 and comprise from 5 to 50% by weight, preferably from 15 to 40% by weight of copper, calculated as CuO, from 50 to 95% by weight, preferably from 60 to 85% by weight, of silicon, calculated as $SiO_2$, from 0 to 20% by weight of magnesium, calculated as MgO, from 0 to 5% by weight of barium, calculated as BaO, from 0 to 5% by weight of zinc, calculated as ZnO, and from 0 to 5% by weight of chromium, calculated as $Cr_2O_3$, in each case based on the total weight of the calcined catalyst, for example the catalyst which is disclosed in EP-A 816 350, page 5, and comprises 30% by weight of CuO and 70% by weight of $SiO_2$.

The hydrogenation or dehydrogenation catalysts used as transalkylation catalyst in the process of the present invention can be prepared by the methods described in the prior art, and some are also commercially available.

In the preparation of supported catalysts, there are no restrictions in respect of the method by which the active components, e.g. nickel, cobalt and/or copper and possibly further components, are applied to the support material used.

In particular, the following application methods are useful:

a) Impregnation application of a metal salt solution to a prefabricated inorganic support in one or more impregnation steps. Subsequent to the impregnation, the support is dried and if necessary calcined.

a1) The impregnation can be carried out by the "incipient wetness" method, in which the support is moistened with an amount of impregnation solution which is not more than the water uptake capacity of the support. However, the impregnation can also be carried out in an excess of solution.

a2) In multistage impregnation processes, it is advantageous to dry and, if appropriate, calcine the material between individual impregnation steps. Multistage impregnation is particularly advantageous when the support is to be loaded with a relatively large amount of metal.

a3) The inorganic support material is preferably used as preshaped material in the impregnation, for example as powder, spheres, extrudates or pellets. Particular preference is given to using powder.

a4) As solvent for the metal salts, preference is given to using concentrated aqueous ammonia.

a5) Promoters can be introduced in a step analogous to a1) by impregnation with an appropriate metal-containing impregnation solution, e.g. a copper-, cobalt- and/or nickel-containing impregnation solution, and a promoter-containing impregnation solution or in a plurality of stages, analogous to a2), by alternate impregnation with metal-containing impregnation solution and promoter-containing impregnation solution.

b) Precipitation

Precipitation of a metal salt solution onto a prefabricated, inert inorganic support. In a particularly preferred embodiment, this is present as powder in an aqueous suspension.

b1) In one embodiment (i), precipitation is carried out using a metal salt solution, preferably a sodium carbonate solution. As substrate, use is made of an aqueous suspension of the support material.

b2) In a further embodiment (ii), the precipitated catalyst can be prepared in a two-stage process. Here, a powder is prepared as described in a) and dried in a first stage. This powder is converted into an aqueous suspension and used as substrate equivalent to that described in embodiment (i).

b3) Promoters can be introduced in a step analogous to b1) by precipitation of a metal-containing solution or in a plurality of steps, analogous to b2), by successive precipitation of a metal-containing solution and promoter-containing solution. In the latter case, the individual precipitations can follow one another directly or can be separated by a washing process and/or drying process and/or calcination process.

As starting substances for a) and/or b), it is in principle possible to use all metal(I) and/or metal(II) salts which are soluble in the solvents used in the application to the support, for example sulfates, nitrates, chlorides, carbonates, acetates, oxalates or ammonium complexes. In a method as described in a), particular preference is given to using metal carbonates, while metal nitrates are particularly preferably used for methods as described in b).

Solids resulting from a) or b) are filtered off in a customary manner and are preferably washed free of alkali.

It is also possible to introduce a promoter component in a suitable form into the filtered and, if appropriate, washed solid. Suitable forms are, for example, inorganic salts or complexes or organic compounds.

Both the end products from a) and those from b) are dried at from 50 to 150° C., preferably from 100 to 140° C., and, if appropriate, subsequently heat treated, for example for a period of 2 hours, at elevated temperature, i.e. generally at from 200 to 400° C., in particular from 200 to 220° C.

It is possible to introduce a promoter component in suitable form either after drying or after heat treatment. Suitable forms are, for example, inorganic salts or complexes or organic compounds. Introduction is advantageously carried out by intensive mixing, kneading and/or compaction, with it being possible to add liquids such as water or alcohols if necessary. Introduction of the promoter component is advantageously followed by a further drying and/or heat treatment step. However, if addition is carried out in the dry state, this may be able to be omitted.

For use in the process of the present invention, the above-described dried powder is preferably shaped to form tablets or similar shaped bodies. As tableting aid for the shaping process, graphite is added, preferably in a proportion of 3% by weight, based on the weight of the dried powder.

The tableted shaped bodies are preferably heated for 2 hours at from 300 to 600° C., in particular from 330 to 350° C. This particular tableting method allows, in contrast to the exclusive use of graphite as tableting aid in customary methods, particularly easy shaping of the powder to form tablets and gives very chemically and mechanically stable catalysts.

It is also possible to introduce a promoter component in a suitable form into the shaped tablets. Suitable forms are, for example, solutions of inorganic salts or complexes or organic compounds. Introduction is advantageously followed by renewed drying at from 50 to 150° C., preferably from 100 to 140° C. In addition, heat treatment can be carried out, preferably for about 2 hours at from 300 to 600° C., in particular from 330 to 350° C.

If the reaction is carried out under transalkylating and simultaneously hydrogenating conditions, in particular in the presence of hydrogen and a transalkylating hydrogenation or dehydrogenation catalyst, preferred transalkylating hydrogenation or dehydrogenation catalysts are the same hydrogenation and dehydrogenation catalysts as described above.

In a continuous transalkylation, the transalkylation catalyst is installed in a tube reactor or a shell-and-tube reactor. In the case of a transalkylating dehydrogenation/hydrogenation reactor and operation in the presence of $H_2$, the catalyst can, if desired, be reduced beforehand by means of hydrogen, but it can be also be started up directly in the presence of the product and hydrogen.

The hydrogen pressure can be in the range from 0 bar to 300 bar, preferably from 1 to 250 bar.

In the case of a reaction in the gas phase, the pressure is generally from 1 to 70 bar.

In the case of a reaction in the liquid phase, the pressure is generally from 70 to 250 bar.

The temperature is generally from 80 to 400° C., in particular from 100 to 350° C., preferably from 120 to 250° C., very particularly preferably from 150 to 250° C.

Depending on the temperature selected, an equilibrium of the alkylamines plus any ammonia, which depends on the ratio of nitrogen to bulkiness and length of the alkyl groups is established. The bulkier the alkyl groups, the smaller the proportion of the corresponding tertiary alkylamine.

The WHSV of the starting material over the catalyst can be from 0.05 to 2 kg of starting material per liter of catalyst and per hour (kg/l*h), preferably from 0.1 to 1 kg/l*h, particularly preferably from 0.2 to 0.6 kg/l*h.

The molar ratio of the amines obtained to one another can vary within a wide range depending on the desired product mix.

After depressurization, the crude product can be distilled.

BRIEF DESCRIPTION OF THE DRAWING(S)

A preferred embodiment of the process of the present invention, in which diethylamine, dibutylamine and/or butylethylamine is/are used as amines, will now be illustrated by way of example with reference to FIG. 1.

Figure 1:
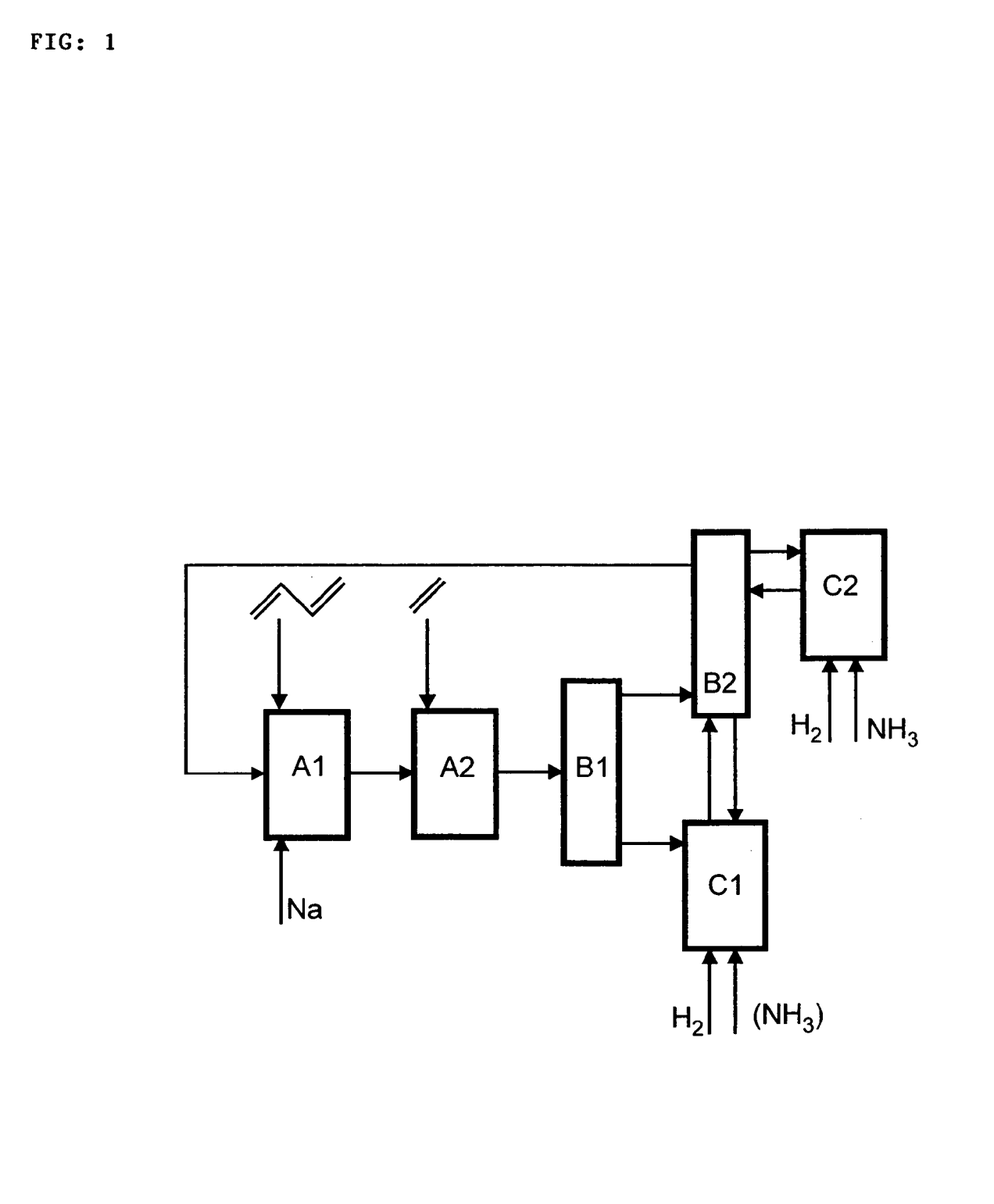

In step (A1), the sodium amide corresponding to the secondary amine used is prepared first. For this purpose, finely dispersed Na is reacted with the amine in an inert solvent, the product amine or in the secondary amine used, with addition of butadiene. The butadiene results in the reaction between the amine and Na taking place to form the amide and thus generate the catalyst species. Further butadiene and the secondary amine then react to form a tertiary amine, namely butenyldiethylamine, butenyldibutylamine and/or butenylbutylethylamine. If only diethylamine is used as amine (preferred embodiment), butenyldiethylamine is formed. The process can be carried out batchwise, semicontinuously or continuously. The temperatures in the reaction are in the range from 0 to 150° C., preferably from 20 to 90° C., in particular from 30 to 70° C., and the pressure is in the range from 1 to 200 bar, preferably from 1 to 100 bar, in particular from 1 to 50 bar.

In process step (A2), the product mixture from step (A1) is then admixed with ethylene, which results in any remaining amine having free H atoms being ethylated. The amount of free amine can be controlled via the relative amount of dialkylamine and butadiene which are reacted in step (A1). Depending on the starting amine, homosubstituted or mixed-substituted amines or mixture thereof are formed. Thus, in the case of dibutylamine as starting material, ethyldibutylamine is formed, in the case of butylethylamine, butyldiethylamine is formed and in the case of diethylamine, triethylamine is formed. Use of a mixture of two or more of the starting materials mentioned makes it possible to obtain a mixture of various fully alkylated amines. Optionally, further dialkylamine starting material(s) or trialkylamine(s) can be added in step (A2) to control the product distribution.

Process step (A2) can be carried out batchwise, semicontinuously or continuously, and the temperature employed in the process is in the range from 30 to 180° C., preferably from 50 to 100° C., while the pressure is in the range from 1 to 200 bar, preferably from 20 to 100 bar, in particular from 30 to 50 bar.

When using dialkylamine as starting material, the conversion can be controlled so that it is up to 100%. However, preference is given to setting the conversion to values of from 10 to 80%, in particular from 30 to 70%.

Optionally, the reaction steps (A1) and (A2) can be combined into a single reaction step (A). In this case, the proportion of butenylations relative to the ethylations is controlled via the concentration, generally the partial pressures, of the two olefins and via the temperature.

After the hydroaminations described, the catalyst is separated off (not shown). This is generally achieved by customary separation methods, for example (vacuum) distillation, membrane filtration, filtration, sedimentation or washing with protic reagents such as $H_2O$, aqueous salt solutions or alcohols. Catalyst which is still intact can be returned to steps (A1) and/or (A2). Unreacted butadiene and/or ethylene and any butene formed can be separated off.

In step (B1), the product mixture is then separated into butyl-/butenyl-containing amines and amines which do not contain butyl or butenyl groups. Thus, butenyldiethylamine, butenyldibutylamine and/or butenylbutylethylamine are separated from the other amines.

These amines are then hydrogenated and isomerized by means of hydrogen in step (C1) using a transalkylating hydrogenation or dehydrogenation catalyst. The amines formed here are butyldiethylamine, dibutylethylamine, tributylamine and/or triethylamine. In general, the mixed-substituted amines containing butyl and ethyl groups, which normally originate from the amine separation (B2), are fed to step (C1). The mixture obtained in (C1) is then passed to the abovementioned step (B2) for fractionation.

Step (B2), which follows step (B1), separates the amine mixture from steps (B1), (C1) and (C2). In this step, when diethylamine, butylethylamine and/or dibutylamine are used in the hydroamination reaction, triethylamine, diethylbutylamine, tributylamine and ethyldibutylamine and also the incompletely alkylated starting amines which, depending on the reaction conditions, may also have been formed in the reaction steps following the amine separation are separated from one another.

In reaction step (C2), a product from the amine separation is isomerized using transalkylation and dehydrogenation/hydrogenation catalysts and with addition of $NH_3$, generally under an $H_2$ atmosphere. In the most preferred embodiment of the present invention, in which diethylamine is used as amine in step (A1), triethylamine is taken from the amine separation (B2). This is, if desired, taken as product from the synthesis circuit, and, if desired, is at least partly isomerized in step (C2) to form a mixture which is rich in diethylamine. This mixture is then recycled to the hydroamination reaction (A1) or (A2). In the other preferred embodiments in which dibutylamine and/or ethylbutylamine are/is used in step (A1) and/or (A2), the product taken from the amine separation may also comprise tributylamine, dibutylamine and mixed-substituted amines which, for example, come from (C1). The product mixture obtained in (C2) is then fractionated, with the amines which are to be used as starting materials in the hydroamination reactions (A1) and/or (A2) being recycled to this step. Product amine is taken from the system. The other amines are returned to the amine separation.

The reaction is preferably carried out so that the net reaction, apart from the catalyst consumption which usually occurs, consumes only hydrogen, ammonia, ethylene and butadiene and gives a mixture comprising monoethylamine, diethylamine and triethylamine and monobutylamine, dibutylamine and tributylamine. The ratio of ethyl to butyl groups in this mixture is in the range from 1:1000 to 1000:1. In general, monoalkylamines, dialkylamines and/or trialkylamines can also be added, in which case these amines are also consumed in the net reaction in addition to the abovementioned components hydrogen, ammonia, ethylene and butadiene. In any case, the process of the present invention is carried out so that in the mass balance >50% of the nitrogen atoms originate from the ammonia, >50% of the ethyl groups originate from ethylene and >50% of the butyl groups originate from butadiene.

The reaction is illustrated by the following examples.

EXAMPLES

Example 1

Sequential Addition of Butadiene and Ethylene onto Diethylamine

All work was carried out under argon; the organic starting materials were dried over molecular sieves before use. The amination was carried out in a 1 l autoclave which had been dried under reduced pressure and flushed with argon before use.

60 mmol of Na were dispersed in 30 ml of n-dodecane at 120° C. by means of an Ultraturrax, and the dispersion was then cooled without stirring (50% by weight of the particles were <60 um). In a sequence of centrifugation, decantation and addition of diethylamine, the dodecane was then mostly replaced by diethylamine. Under a gentle stream of argon, a dispersion of 60 mmol of sodium in 6 mol of diethylamine was placed in the reactor, the reactor was closed, heated to 50° C. and 131 g of 1,3-butadiene as gas were dissolved in the dispersion over a period of 4 hours while stirring. The introduction of butadiene was then stopped, the contents of the autoclave were heated to 70° C. and the autoclave was pressurized with 40 bar of ethene. After the reaction was complete, the contents of the reactor were washed with 10 ml of 50% strength KOH solution in $H_2O$, the organic phase was separated off and dried. The composition of the reaction mixture determined by gas chromatography is shown in Table 1.

TABLE 1

Hydroamination of butadiene and ethylene by diethylamine

| Species | B1a | B1b1 | B1b2 | B1b3 | B1b4 | B1c |
|---|---|---|---|---|---|---|
| Time from addition of ethylene | — | 0.5 h | 1 h | 2 h | 4 h | 6 h |
| Diethylamine | 36.85 | 26.34 | 22.39 | 19.18 | 15.17 | 15.67 |
| Triethylamine | — | 5.14 | 9.58 | 14.60 | 20.29 | 22.07 |
| Butenyldiethylamine* | 60.27 | 65.63 | 65.03 | 63.17 | 61.70 | 59.42 |

*cis-1-, trans-1-, cis-2-, trans-2- and 3-butenyldiethylamine

Example 2

Sequential Addition of Butadiene and Ethylene onto Diethylamine and Dibutylamine The experiment was carried out as described in Example 1, but the Na was dispersed directly in di-n-butylamine (50% by weight of the particles were <150 μm). 1.5 mol of di-n-butylamine and 3 mol of diethylamine were used as starting amines, and 81 g instead of 131 g of 1,3-butadiene were added. The composition of the reaction mixture determined by gas chromatography is reported in Table 2.

TABLE 2

Hydroamination of butadiene and ethylene by diethylamine

| Species | B2a | B2b1 | B2b2 | B2b3 | B2b4 | B2c |
|---|---|---|---|---|---|---|
| Time from addition of ethylene | — | 0.5 h | 1 h | 2 h | 4 h | 6 h |
| Diethylamine | 20.21 | 12.97 | 11.52 | 9.25 | 8.24 | 7.60 |
| Triethylamine | — | 2.57 | 4.76 | 7.34 | 10.28 | 11.45 |
| Butenyldiethylamine* | 32.74 | 32.84 | 32.33 | 31.78 | 31.27 | 30.83 |
| Dibutylamine | 30.96 | 30.86 | 28.92 | 26.49 | 23.71 | 22.48 |
| Ethyldibutylamine | — | 2.09 | 3.93 | 6.58 | 9.03 | 10.21 |
| Butenyldibutylamine* | 13.16 | 15.69 | 15.44 | 15.43 | 14.58 | 14.60 |

*cis-1-, trans-1-, cis-2-, trans-2- and 3-butenyldiethylamine and -dibutylamine

Example 3

Simultaneous Addition of Butadiene and Ethylene onto Diethylamine and Dibutylamine The experiment was carried out as described in Example 2, but a mixture of 2 mol % of butadiene and 98 mol % of ethylene was added at 40 bar and 70° C. to the dispersion of Na and the amines. The composition of the reaction mixture determined by gas chromatography is reported in Table 3.

TABLE 3

Hydroamination of butadiene and ethylene by diethylamine (single-vessel reaction)

| Species | B3b1 | B3b2 | B3b3 | B3b4 | B3c |
|---|---|---|---|---|---|
| Time from addition of gas | 0.5 h | 1 h | 2 h | 4 h | 6 h |
| Diethylamine | 35.63 | 28.84 | 22.65 | 15.52 | 12.02 |
| Triethylamine | 3.01 | 5.54 | 8.02 | 10.91 | 12.19 |
| Butenyldiethylamine* | 7.65 | 13.76 | 19.12 | 25.47 | 28.92 |
| Dibutylamine | 44.27 | 36.64 | 30.39 | 23.57 | 21.36 |
| Ethyldibutylamine | 2.00 | 3.94 | 6.26 | 8.08 | 8.35 |
| Butenyldibutylamine* | 3.44 | 6.60 | 10.61 | 14.20 | 15.15 |

*cis-1-, trans-1-, cis-2-, trans-2- and 3-butenyldiethylamine and -dibutylamine

Example 4

Hydrogenative Transalkylation of Butenyldiethylamine

Diethylbutenylamine resulting from the addition of diethylamine onto butadiene was, in pure form or as a mixture with triethylamine, passed continuously at 10 bar through a tube reactor. Two catalysts were employed:
Catalyst 1: 52% CuO, 10% NiO, balance $Al_2O_3$
Catalyst 2: 10% CoO, 10% NiO, 4% CuO, balance $Al_2O_3$
Both catalysts were heated to 280° C. under a hydrogen atmosphere prior to the reaction.

At a pressure of 10 bar and 220° C., the starting materials were brought into the gas phase. The composition of the reaction mixture determined by gas chromatography is reported in Table 4.

TABLE 4

Transalkylation of diethylbutenylamine

| Cat. | Temp in ° C. | Pressure in bar | Ammonia mol/h | Ammonia g/h | BDEA mol/h | BDEA ml/h | $NH_3$/BDEA Mol/mol | WHSV kg/l*h | $H_2$ [nl/h] | MEA RT = 3.37 | DEA RT = 5.61 |
|---|---|---|---|---|---|---|---|---|---|---|---|
| Starting Material: BDEA | | | | | | | | | | | |
| 1 | 220 | 10 | 0.2835 | 4.8 | 0.0945 | 15.8 | 3/1 | 0-2 | 10 | — | 9.78 |
| 1 | 220 | 10 | 0.4725 | 8 | 0.0945 | 15.8 | 5/1 | 0.2 | 10 | — | 9.48 |
| Starting material: mixture of TEA + BDEA, 2:1 mol/mol | | | | | | | | | | | |
| 1 | 220 | 10 | 0.4725 | 8 | | 15.8 | 5/1 | 0.2 | 10 | 24.11 | 37.99 |
| 1 | 220 | 10 | 0.2835 | 4.8 | | 15.8 | 3/1 | 0.2 | 10 | 15.06 | 36.66 |
| Starting Material: BDEA | | | | | | | | | | | |
| 2 | 190 | 10 | | | 0.0945 | 15.8 | | 0.2 | 10 | — | 4.64 |
| 2 | 200 | 10 | | | 0.0945 | 15.8 | | 0.2 | 10 | — | 6.52 |
| 2 | 210 | 10 | | | 0.0945 | 15.8 | | 0.2 | 10 | 1.42 | 13.83 |
| 2 | 220 | 10 | | | 0.0945 | 15.8 | | 0.2 | 10 | 6.84 | 17.55 |

| Cat. | MBuA RT = 7.3 | TEA RT = 8.65 | EtBuA RT = 10.63 | DEtBuA RT = 12.66 | DBuA RT = 14.38 | EtDBuA RT = 15.53 | TBuA RT = 17.78 | Total |
|---|---|---|---|---|---|---|---|---|
| 1 | — | 22.64 | 11.51 | 34.34 | 3.27 | 15.28 | 2.07 | 98.88 |
| 1 | — | 22.97 | 10.93 | 34.57 | 3.06 | 15.01 | 2.05 | 98.06 |
| 1 | 4.56 | 12.99 | 12.37 | 5.55 | 1.11 | 0.96 | — | 99.64 |
| 1 | 3.11 | 19.79 | 13.68 | 9.17 | 1.20 | 1.32 | — | 99.99 |
| 2 | — | 11.88 | 6.65 | 64.43 | 1.49 | 9.62 | 1.28 | 99.98 |

TABLE 4-continued

Transalkylation of diethylbutenylamine

| 2 | —    | 14.84 | 9.13  | 52.75 | 2.49 | 12.35 | 1.84 | 99.92 |
| 2 | 1.14 | 17.36 | 16.34 | 30.96 | 4.65 | 12.15 | 1.78 | 99.64 |
| 2 | 4.55 | 8.62  | 18.92 | 11.14 | 4.97 | 4.75  | 0.72 | 78.06 |

BDEA: butyldiethylamine
MEA: monoethylamine
DEA: diethylamine
TEA: triethylamine
EtBuA: ethylbutylamine
DEtBuA: diethylbutylamine
DBuA: dibutylamine
EtDBuA ethyldibutylamine
TBuA: tributylamine

Example 5

Hydrogenative Transalkylation of the Reaction Mixture from Example 2

The reaction product mixture from Example 2 was passed continuously at 10 bar through a tube reactor. Catalyst 2 was used:

This was heated to 280° C. under a hydrogen atmosphere prior to the reaction. The mixture was hydrogenated at a pressure of 10 bar and 155° C. The reaction with ammonia was carried out at 210° C. The composition of the reaction mixture determined by gas chromatography is reported in Table 5.

TABLE 5

Transalkylation of the amine product mixture from Example 2

| Temp in ° C. | Pressure in bar | Ammonia mol/h | g/h | BDEA mol/h | $NH_3$/BDEA ml/mol h | WHSV kg/l*h | $H_2$ [nl/h] | MEA RT = 3.37 | DEA RT = 5.61 | MBuA RT = 7.3 |
|---|---|---|---|---|---|---|---|---|---|---|
| 155 | 2  |       |     | 0.089 | 12 |       | 0.15 | 10 | —     | 8.78  | 0.28  |
| 210 | 10 | 0.135 | 2.3 | 0.089 | 12 | 1.5/1 | 0.15 | 10 | 7.89  | 14.26 | 9.65  |
| 210 | 10 | 0.229 | 3.9 | 0.089 | 12 | 2.5/1 | 0.15 | 10 | 10.02 | 14.75 | 11.79 |
| 210 | 10 | 0.447 | 7.6 | 0.089 | 12 | 5/1   | 0.15 | 10 | 16.95 | 13.75 | 17.93 |

| Temp in ° C. | TEA RT = 8.65 | EtBuA RT = 10.63 | DEtBuA RT = 12.66 | DBuA RT = 14.38 | EtDBuA RT = 15.53 | TBuA RT = 17.78 | Total |
|---|---|---|---|---|---|---|---|
| 155 | 12.49 | 4.99  | 23.02 | 8.39  | 13.46 | 28.58 | 99.99 |
| 210 | 4.9   | 27.31 | 11.44 | 12.91 | 9.14  | 2.49  | 99.99 |
| 210 | 4.26  | 26.83 | 9.19  | 13.01 | 7.47  | 2.67  | 99.99 |
| 210 | 2.63  | 25.21 | 5.69  | 11.77 | 4.67  | 1.38  | 99.98 |

BDEA: butyldiethylamine
MEA: monoethylamine
DEA: diethylamine
TEA: triethylamine
EtBuA: ethylbutylamine
DEtBuA: diethylbutylamine
DBuA: dibutylamine
EtDBuA ethyldibutylamine
TBuA: tributylamine Example 6

Hydroyenative Transalkylation of Triethylamine

Triethylamine was passed continuously through a tube reactor. Two catalysts were used:
The catalyst (52% CuO, 10% NiO, balance $Al_2O_3$) was heated to 280° C. under a hydrogen atmosphere prior to the reaction. The composition of the reaction mixture (in % by weight) is shown in Table 6.

TABLE 6

Transalkylation of triethylamine

| Feeds | | | | | Temperature | | Pressure | Analysis | | |
|---|---|---|---|---|---|---|---|---|---|---|
| Triethylamine | Ammonia | Hydrogen | Molar ratio | WHSV | in ° C. | | | | | |
| in ml/h | g/h | standard l/h | Of $NH_3$/TEA | in kg/l*h | Preheater | Oven | in bar | MEA | DEA | TEA |
| 330 | 160 | 300 | 3.9 | 0.40 | 200 | 200 | 50 | 19.64 | 51.93 | 28.43 |
| 330 | 160 | 300 | 3.9 | 0.40 | 180 | 180 | 50 | 14.29 | 39.29 | 46.42 |
| 330 | 160 | 300 | 3.9 | 0.40 | 220 | 220 | 50 | 21.19 | 52.82 | 26.00 |
| 330 | 160 | 300 | 3.9 | 0.40 | 170 | 170 | 50 | 12.39 | 35.04 | 52.57 |
| 330 | 160 | 300 | 3.9 | 0.40 | 180 | 180 | 30 | 9.85 | 38.74 | 51.40 |
| 330 | 160 | 300 | 3.9 | 0.40 | 180 | 180 | 70 | 14.38 | 36.56 | 49.06 |
| 490 | 240 | 300 | 4.0 | 0.60 | 180 | 180 | 50 | 13.71 | 36.92 | 49.37 |
| 490 | 240 | 300 | 4.0 | 0.60 | 200 | 200 | 50 | 19.44 | 50.96 | 29.60 |
| 490 | 240 | 300 | 4.0 | 0.60 | 220 | 220 | 50 | 21.46 | 52.84 | 25.70 |
| 660 | 320 | 300 | 3.9 | 0.80 | 200 | 200 | 50 | 18.52 | 50.62 | 30.87 |
| 660 | 320 | 300 | 3.9 | 0.80 | 220 | 220 | 50 | 21.75 | 52.75 | 25.50 |

We claim:

1. A process for preparing ethylamines, butylamines and mixed ethyl/butylamines, which comprises the following steps:
   (i) hydroamination of butadiene and ethylene by means of a monoalkylamine and/or dialkylamine in which alkyl-ethyl and/or butyl in the presence of an alkali metal amide as catalyst,
   (ii) isomerization of the amines obtained in the hydroamination (i), optionally under the following conditions:
      (iia) prior fractionation into particular fractions and/or
      (iib) isomerization under hydrogenating conditions and/or
      (iic) isomerization in the presence of ammonia,
   (iii) fractionation of the resulting product mixture with isolation of the desired product amines and recycle of the amines suitable as starting material to step (i) and, if desired, to step (ii).

2. A process as claimed in claim 1, wherein the hydroamination (i) is carried out so that the starting materials necessary for preparing the preferred product or products are added in such amounts that the preferred product or products are formed in predominant amounts.

3. A process as claimed in claim 1, wherein diethylamine, dibutylamine or ethylbutylamine are used in the hydroamination reaction (i).

4. A process as claimed in claim 1, wherein diethylamine is used in the hydroamination reaction.

5. A process as claimed in claim 1, wherein diethylamine and an excess of ethylene are used in the hydroamination reaction and the main product obtained is triethylamine.

6. A process as claimed in claim 5, wherein triethylamine is obtained in a 5 to 20 fold excess, over butyl-/butenyl-containing olefins.

7. A process as claimed in claim 5, wherein triethylamine is obtained in a 8 to 12 fold excess, over butyl-/butenyl-containing olefins.

8. A process as claimed in claim 1, wherein the reaction mixture obtained in the hydroamination (i) is separated in step (iia) into butenyl-containing amines and amines which do not contain butenyl groups and the fractions obtained are separately isomerized and/or hydrogenated.

9. A process as claimed in claim 1, wherein the alkali metal amide is an amide of Na.

10. A process as claimed in claim 9, wherein the amide is from the group consisting of diethylamide, dibutylamide and ethylbutylamide.

11. A process as claimed in claim 9, wherein the amide is diethylamide.

12. A process as claimed in claim 9, wherein the metal amide is prepared from the amine which is reacted with the olefin in the hydroamination reaction.

13. A process as claimed in claim 12, wherein the metal amide is prepared from the amine by reaction with the corresponding alkali metal in the presence of butadiene.

14. A process as claimed in claim 13, wherein the metal amide is prepared in situ in the hydroamination reaction (i).

15. A process as claimed in claim 1, wherein the starting amine or amines is/are reacted firstly with butadiene and then with ethylene in the hydroamination (i).

16. A process as claimed in claim 15, wherein the reactants are reacted in a single stage reaction.

17. A process as claimed in claim 16, wherein the reactants are reacted in a single stage reaction with simultaneous formation of the metal amide.

18. A process as claimed in claim 1, wherein amines containing butyl and/or butenyl groups are separated off in step (iia) and are subsequently hydrogenated and isomerized with transalkylation in step (ii), in the presence or absence of NH$_3$ to form primary and secondary butyl-containing amines.

19. A process as claimed in claim 1, wherein the mixture obtained after the butyl-/butenyl-subsituted amines have been separated off, which comprises triethylamine, diethylamine and possibly monoethylamine, is fractionated to give the desired product, and all or some of the desired product is taken from the process and another mixture is separated off and is recycled either directly of after isomeriziag transalkylation as starting material to the hydroamination reaction.

20. A process as claimed in claim 19, wherein the desired product is triethylamine.

21. A process as claimed in claim 1, wherein step (ii) is carried out in the presence of dehydration catalysts and hydrogenation/dehydrogenation catalysts which comprise elements selected from the group consisting of copper, silver, gold, iron, cobalt, nickel, rhenium, ruthenium, rhodium, palladium, osmium, iridium, platinum, chromium, molybdenum and tungsten either in metallic form or in the form of compounds which are reduced to the corresponding metal under the process conditions as catalytically active constituents.

22. A process as claimed in claim 21, wherein the catalysts comprise a support material selected from the group consisting of aluminum oxide, zirconium oxide, titanium oxide, carbon and/or silicon dioxide.

23. A process as claimed in claim 1, where one or more of the step (ii) reactions are carried out in the presence of hydrogen or Nh$_3$.

24. A process for preparing ethylamines and butylamines, wherein butadiene, ethylene, hydrogen, ammonia and monoalkylamine, dialkylamine and/or trialkylamine in which the alkyl=ethyl or butyl are reacted with one another in the presence of amide catalysts to give a mixture which comprises monoethylamine, diethylamine, triethylamine, monobutylamine, dibutylamine and tributylamine and in which the ratio of the ethyl groups to the butyl groups is in the range from 1:1000 to 1000:1, and in the mass balance >50% of the nitrogen atoms originate from the ammonia, >50% of the ethyl groups originate from ethylene, and >50% of the butyl groups originate from butadiene.

25. A process as claimed in claim 24, wherein the reaction is carried out so that only hydrogen, ammonia, ethylene and butadiene are consumed, and a mixture comprising monoethylamine, diethylamine, triethylamine, monobutylamine, dibutylamine and tributylamine is obtained.

* * * * *

UNITED STATES PATENT AND TRADEMARK OFFICE
CERTIFICATE OF CORRECTION

| | | |
|---|---|---|
| PATENT NO. | : 7,161,039 B2 | Page 1 of 1 |
| APPLICATION NO. | : 10/495278 | |
| DATED | : January 9, 2007 | |
| INVENTOR(S) | : Steinbrenner et al. | |

It is certified that error appears in the above-identified patent and that said Letters Patent is hereby corrected as shown below:

Column 24, indicated line 6, "$Nh_3$" should read --$NH_3$--

Signed and Sealed this

Tenth Day of July, 2007

JON W. DUDAS
*Director of the United States Patent and Trademark Office*